US010500217B2

(12) United States Patent
Matthews et al.

(10) Patent No.: US 10,500,217 B2
(45) Date of Patent: Dec. 10, 2019

(54) VITAMIN D₃, HEAT SHOCK PROTEINS, AND GLUTATHIONE FOR THE TREATMENT OF CHRONIC INFLAMMATION AND CHRONIC DISEASES

(71) Applicants: Leslie Ray Matthews, East Point, GA (US); Alexzander Asea, Perrysburg, OH (US)

(72) Inventors: Leslie Ray Matthews, East Point, GA (US); Alexzander Asea, Perrysburg, OH (US)

(73) Assignee: LESLIE RAY MATTHEWS, M.D., LLC, East Point, GA (US)

( * ) Notice: Subject to any disclaimer, the term of this patent is extended or adjusted under 35 U.S.C. 154(b) by 0 days.

(21) Appl. No.: 15/967,516

(22) Filed: Apr. 30, 2018

(65) Prior Publication Data

US 2019/0328754 A1    Oct. 31, 2019

(51) Int. Cl.

| | |
|---|---|
| *A61K 31/593* | (2006.01) |
| *A61K 9/20* | (2006.01) |
| *A61K 9/48* | (2006.01) |
| *A61P 9/04* | (2006.01) |
| *A61P 25/28* | (2006.01) |
| *A61P 11/08* | (2006.01) |
| *A61K 38/06* | (2006.01) |
| *A61K 39/00* | (2006.01) |

(52) U.S. Cl.
CPC .............. *A61K 31/593* (2013.01); *A61K 9/20* (2013.01); *A61K 9/4825* (2013.01); *A61P 9/04* (2018.01); *A61P 11/08* (2018.01); *A61P 25/28* (2018.01); *A61K 38/063* (2013.01); *A61K 2039/6043* (2013.01); *A61K 2300/00* (2013.01)

(58) Field of Classification Search
None
See application file for complete search history.

(56) References Cited

U.S. PATENT DOCUMENTS

| 6,964,969 B2 | 11/2005 | McCleary |
| 7,754,769 B2 | 7/2010 | Kubow et al. |
| 9,023,402 B2 | 5/2015 | Haas et al. |
| 2004/0266676 A1 | 12/2004 | Yasuda |
| 2011/0059917 A1 | 3/2011 | Jimenez et al. |
| 2011/0229585 A1 | 9/2011 | Kaiser |
| 2012/0015046 A9 | 1/2012 | Giordano et al. |
| 2017/0196949 A1 | 7/2017 | Essen-Möller et al. |

FOREIGN PATENT DOCUMENTS

| EP | 1459762 A1 | 9/2004 |
| EP | 3213767 A1 | 9/2017 |
| JP | 5787285 B2 | 9/2015 |
| WO | 2012097255 A2 | 7/2012 |
| WO | 2017178029 A1 | 10/2017 |

OTHER PUBLICATIONS

Matthews, IJCRI 2013; 4(3):143-149 (Year: 2013).*
Pittet, J Trauma., 2002;52:611-617 (Year: 2002).*
Alexander A.A. Asea, Antonio De Maio (eds.), Heat Shock Proteins: Potent Mediators of Inflammation and Immunity, 2007, p. 357, vol. 1, Springer Nature, Dordrecht, Netherlands.
Stuart K. Calderwood, Michael Y. Sherman, Daniel R. Ciocca (Eds.), Heat Shock Proteins in Cancer, 2007, p. 398, vol. 2, Springer Nature, Dordrecht, Netherlands.
Alexander A.A. Asea, Ian R. Brown (Eds.), Heat Schock Proteins and the Brain: Implications for Neurodegenerative Diseases and Neuroprotection, 2008, p. 373, vol. 3, Springer Nature, Dordrecht, Netherlands.
A. Graham Pockley, Stuart K. Calderwood, M. Gabriella Santoro, (Eds.), Prokaryotic and Eukaryotic Heat Shock Proteins in Infectious Disease, 2009, p. 311, vol. 4, Springer Nature, Dordrecht, Netherlands.
Alexander A.A.Asea, Bente K Pedersen (Eds.), Heat Schock Proteins and Whole Body Physiology, 2010, p. 429, vol. 5, Springer Nature, Dordrecht, Netherlands.
Robert M. Tanguay, Lawrence E Hightower (Eds.), The Big Book on Small Heat Shock Proteins, 2015, p. 682, vol. 8, Springer Nature, Dordrecht, Netherlands.
A. A. A. Asea, N. N. Almasoud, S. Krishnan, P. Kaur (Eds.), Heat Shock Protein-Based Therapies, 2015, p. 375, vol. 9, Springer Nature, Dordrecht Netherlands.
Alexzander A. A. Asea, Punit Kaur (Eds.), Heat Shock Proteins in Veterinary Research and Medicine, 2018, p. 398, vol. 12, Springer Nature, Dordrecht Netherlands.
Alexzander A. A. Asea, Punit Kaur (Eds.), Regulation of Heat Shock Protein Responses, 2018, p. 501, vol. 13, Springer Nature, Dordrecht Netherlands.
Y. Ahmed, D.D. Griggs, O.K. Danner, R. Matthews, K. L. Wilson, Worsening severity of vitamin D deficiency is associated with increased length of stay, surgical intensive care unit cost, and mortality rate in surgical intensive care unit patients, The American Journal of Surgery, Jul. 2012, pp. 37-43, vol. 204, Issue 1.
Alexzander A. A. Asea, Stuart K. Calderwood, Punit Kaur (Eds.), Heat Shock Protein and Plants, 2016, vol. 10, Springer Nature, Dordrecht Netherlands.
Jill Butterfield, Thomas P. Lodise Jr., Manunath P. Pai, Applications of Pharmacokinetic and Pharmacodynamic Principles to Optimize Drug Dosage Selection Example of Antibiotic Therapy Management, 2012, Chapter 9, Therapeutic Drug Monitoring: Newer Drugs and Biomarkers.

(Continued)

*Primary Examiner* — Satyanarayana R Gudibande

(74) *Attorney, Agent, or Firm* — Angela J. Grayson; Precipice IP, PLLC

(57) ABSTRACT

The present disclosure is directed to co-administration of high dose Vitamin D₃, heat shock proteins, glutathione, and kits provided for co-administration of these compositions, for the treatment of patients with chronic inflammation and chronic diseases.

10 Claims, No Drawings

Specification includes a Sequence Listing.

(56) References Cited

OTHER PUBLICATIONS

Alexzander Asea, Stine-Kathrein Kraeft, Evelyn A. Kurt-Jones, Mary Ann Stevenson, Lan Bo Chen, Robert W. Finberg, Gloria C. Koo, & Stuart K. Calderwood, HSP70 stimulates cytokine production through a CD14-dependant pathway, demonstrating its dual role as a chaperone and cytokine, Apr. 2000, Chapter 4, vol. 6, Nature Medicine, Nature America, Inc.
Alexander A. A. Asea, Fabiana Geraci, Punit Kaur (Eds.), Multiple Sclerosis: Bench to Bedside Global Perspectives on a Silent Killer, Advances in Experimental Medicine and Biology 958, 2017, Springer Nature, Cham Switzerland.
Jill E. Maddison, Stephen W. Page, Timothy M. Dyke, Clinical pharmacokinetics, Pharmacokinetics and the Veterinary Clinician, Chapter 2.
V. Lobo, A. Patil, A. Phatak, N. Chandra, Free radicals, antioxidants and functional foods: Impact on human health, Pharmacognosy Review, Jul.-Dec. 2010, Chapters 4(8), pp. 118-126, Wolters Kluwer—Medknow Publications.
L. Ray Matthews, Yusuf Ahmed, Omar Danner, Carolyn Moore, Carl Lokko, Jonathan Nguyen, Keren Bashan-Gilzenrat, Diane Dennis Griggs, Nekelisha Prayor, Peter Rhee, Ed Childs, Kenneth Wilson, High Dose Vitamin D, Digoxin, and BiDil Reverse Congestive Heart Failure in a Critically Ill Trauma Patient and a Severely Obese Male Patient, Global Journal of Medical and Clinical Case Reports, Apr. 2017, ISSN: 2455-5282, Peertechz Publications Pvt. Ltd.
HSP90AA1 heat shock protein 90 alpha family class A member 1 [*Homo sapiens* (human)], HGNC: 5523, HSP90AA1, Jul. 2018, HGNC.
HSPA1A heat shock protein family A (Hsp70) member 1A [*Homo sapiens* (human)], HGNC: 5233, HSPA1A, Jul. 2018, HGNC.
HSPB1 heat shock protein family B (small) member 1 [*Homo sapiens* (human)], HGNC: 5246, HSPB1, Jul. 2018, HGNC.
HSPD1 heat shock protein family D (Hsp60) member 1 [*Homo sapiens* (human)], HGNC: 5261, HSPD1, Jul. 2018, HGNC.
Bryan Davis, Indianola native takes research to the SEC, The Enterprise-Tocsin, Jan. 4, 2018, p. 12, vol. CXXXII No. 1, Indianola, MS.
Rommel G.Tirona, Richard B. Kim, Introduction to Clinical Pharmacology, Human Pharmacology, 2009, Chapter 2, Clinical and Translational Science, Elsevier Inc.
Leslie Ray Matthews MD, Albert Nelson Marquis, Leslie Ray Matthews, MD, Presented with the Albert Velson Marquis Lifetime Achievement Award by Marquis Who's Who, Marquis Who's Who, Feb. 15, 2018, Marquis Publications.
Dr. L. Ray Matthews Unleashes the Power of Vitamin D, Oct. 2013.
Jurgen Steinmeyer, Pharmacological basis for the therapy of pain and inflammation with nonsteroidal anti-Inflammatory drugs, Arthritis Research & Therapy, 20001:379, Jul. 2000, Current Science Ltd.
Leslie Ray Matthews MD FACS, Kenneth Wilson MD FACS, Yusef Ahmed MD FACS, Diane Griggs VP, Ed Childs MD FACS, Omar Danner MD FACS, Severe vitamin D deficiency is associated with worsened Dutcomes in surgical patients with ventilated-associated pneumonia, Journal of the American College of Surgeons, Sep. 2012, p. 867, vol. 215, Issue 3 Supplement.
Gale E. Smith, Max D. Summers, M. J. Fraser, Production of Human Beta Interferon in Insect Cells Infected with a Baculovirus Expression Vector, Mollecular and Cellular Biology, Dec. 1983, pp. 2156-2165, vol. 3, No. 12, American Society for Microbiology.
Ward Lutz, Kenji Kohno, Rajiv Kumar, The Role of Heat Shock Protein 70 in Vitamin D Receptor Function, Biochemical and Biophysical Research Communications 282, 2001, pp. 1211-1219, Ideal Library.
DR Matthews, High levels of antibiotic resistance found worldwide, new data show, Top News in Internal Medicine, Jan. 29, 2018, #10 of 21, MDLinx.
Barbara Prietl, Gerlies Treiber, Thomas R Pieber, Karin Amrein, Vitamin D and Immune Function, gutrients, Jul. 2013, pp. 2502-2521, Issue 2072-6643, MDPI, Basel, Switzerland.
Khan A., Dawoud H., Malinski T., Vitamin D3 backed to prevent and repair heart damage,Study says adequate sunlight exposure is vital, International Journal of Nanomedicine, https://doi.org/10.2147/IJN.S152822.
Barbara Prietl, Gerlies Treiber, Thomas R. Pieber, Karin Amrein, Vitamin D and Immune Function, Nutrients, Jul. 5, 2013, pp. 2502-2521, vol. 7, MDPI, Basel, Switzerland.
L. Ray Matthews, Yusuf Ahmed, Omar K. Danner, Golda Kwaysi, Dianne Dennis-Griggs, Keren Aviva Bashan-Gilzenrat, Jonathan Nguyen, Ed W. Childs, Nekelisha Prayor, Peter Rhee, Kenneth L. Wilson, Vitamin D, Glutamine, Evidence-Based Medicine, and Close Staff Supervision Reduce Mortality Rate at a Level I Trauma Center, Global Journal of Medical and Clinical Case Reports, Mar. 9, 2017, pp. 20-24, ISSN: 2455-5282, Peertechz Publications Pvt. Ltd.
James Chong, Vitamin D may help prevent heart failure after heart attack, Westmed Institute for Medical Research, Mar. 8, 2018, p. 1 of 3, Medicalexpress.com.
Narasimha Swamy, Scott C. Mohr, Wenrong, Rahul Ray, Vitamin D Receptor Interacts with DnaK/Heat Shock Protein 70: Identification of DnaK Interaction Site on Vitamin D Receptor, Archives of Biochemistry and Biophysics, Mar. 15, 1999, pp. 219-226, vol. 363, No. 2.
Brian J. Rebolledo M.D., Johnathan a Bernard M.D., Brian C. Werner M.D., Andrea K Finlay Ph.D., Benedict U. Nwachukwu M.D M.B.A., David M. Dare M.D., Russell F. Warren M.D., Scott F. Rodeo M.D., The Association of Vitamin D Status in Lower Extremity Muscle Strains and Core Muscle Injuries at the National Football League Combine, Article in Press, 2017, pp. 1-6, The Journal of Arthroscopic Related Surgery.
Hongying Zheng, Ganachari M. Nagaraja, Punit Kaur, Edwina E. Asea, Alexzander Asea, Chaperokine Function of Recombinant Hsp72 Produced in Insect Cells Using a Baculovirus Expression System Is Retained, The Journal of Biological Chemistry, Jan. 1, 2010, pp. 349-356, vol. 285, No. 1, JCB Papers in Press, USA.
International Searching Authority/US, International Search Report and Written Opinion for PCT/US19/29692, dated Sep. 10, 2019, 14 pages.

* cited by examiner

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccattgtaat gagacgcac                                                    19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgtaaatca acaacgcaca g                                                 21
```

VITAMIN D₃, HEAT SHOCK PROTEINS, AND GLUTATHIONE FOR THE TREATMENT OF CHRONIC INFLAMMATION AND CHRONIC DISEASES

SEQUENCE LISTING

The instant application contains a Sequence Listing which has been submitted electronically in ASCII format and is hereby incorporated by reference in its entirety. Said ASCII copy, created on Jun. 15, 2018, is named 2017-12-00152PA_SL.txt and is 792 bytes in size.

FIELD OF THE DISCLOSURE

The present disclosure relates to novel methods of co-administration of high dose Vitamin $D_3$, heat shock proteins, glutathione, and kits provided for co-administration of these compositions, for the treatment of patients with chronic inflammation and chronic diseases.

BACKGROUND OF THE DISCLOSURE

Nearly half of all Americans suffer from at least one chronic disease. More than two-thirds of all deaths are caused by one or more of five chronic diseases: heart disease, cancer, stroke, chronic obstructive pulmonary disease, and diabetes. More than one in four Americans have multiple chronic conditions, and evidence is growing that the presence of one chronic condition has a negative impact on the risk of developing others, particularly as people age.

Chronic disease affects health and quality of life, but it is also a major driver of health care costs and has a related impact on business, such as absenteeism. According to the Centers for Disease Control and Prevention, chronic disease accounts for approximately 75 percent of the nation's aggregate health care spending—or an estimated $5,300 per person in the U.S. each year. In terms of public insurance, treatment of chronic disease constitutes an even larger proportion of spending; 96 cents per dollar for Medicare and 83 cents per dollar for Medicaid.

Chronic diseases generally cannot be prevented by vaccines or cured by medication, nor do they just disappear. Most available treatments and medications only treat the symptoms and do not address the underlying problems, which are chronic inflammation and free oxygen radical formation, for example U.S. Pat. No. 8,507,219 and J. Steinmeyer. *Pharmacological Basis for the Therapy Of Pain And Inflammation With Nonsteroidal Anti-Inflammatory Drugs*. Arthritis Research 2000; 2(5), 379-385. As a result, existing treatments and medications have many side effects. Therefore, a need remains for therapeutic options for chronic diseases and inflammation with minimal side effects but high efficacy.

The inventors have surprisingly found that high dose Vitamin $D_3$, heat shock proteins, and glutathione work synergistically to reduce chronic inflammation and free radical formation, which are associated with diseases of chronic aging. Together, these three agents are the most powerful substances in the human body, and they have never been used together to combat chronic inflammation and chronic diseases of aging.

SUMMARY OF THE DISCLOSURE

The present disclosure provides novel methods of co-administration of high dose Vitamin $D_3$, heat shock proteins, and glutathione.

The present disclosure includes methods of co-administering the compositions described herein to patients, together or in any order, for the treatment of chronic inflammation and chronic diseases such as traumatic brain injury; concussion; congestive heart failure; coronary artery disease; heart attacks; stroke; chronic neurogenic disorders; arthritis; acute respiratory distress syndrome; community acquired pneumonia; ventilated associated pneumonia; dementia; Alzheimer's Disease; acute and chronic renal failure; multi-system organ failure; acute and chronic liver diseases, chronic obstructive pulmonary disease, acute and chronic pulmonary diseases, auto-immune diseases, cancers, cardiopulmonary arrest, and other chronic diseases of aging.

The compositions of the present disclosure may be oral dosage forms, including tablets, capsules and gel capsules. Choice in dosage form promotes ease of administration and compliance with dosing regimens.

The present disclosure is also directed to kits that may be provided, wherein the compositions as described herein are packaged for co-administration to a patient.

DETAILED DESCRIPTION OF THE DISCLOSURE

It is understood that the present disclosure is not limited to the particular methodologies, protocols, etc., described herein, as these may vary. It is also understood that the terminology used herein is used for the purpose of describing particular embodiments only and is not intended to limit the scope of the present disclosure.

Unless defined otherwise, all technical and scientific terms used herein have the same meanings as commonly understood by one of ordinary skill in the relevant art. Specific methods, devices, and materials are described, although any methods and materials similar or equivalent to those described herein can be used in the practice or testing of the present disclosure.

As used herein and unless otherwise specified, the terms "about" when located before a dosage amount or dosage range of a specific ingredient, refers to an amount or range closely above and/or closely below the stated amount or range that does not manifestly alter the therapeutic effect of the specific ingredient from the stated amount or range.

As used herein and unless otherwise specified, the term "co-administration" and "co-administering" refers to the administration of two compositions to a patient within a certain desired time. "Administering" refers to the act of giving a composition to a patient or otherwise making such composition available to a patient or the patient taking a composition.

As used herein and unless otherwise specified, the term "dosage form" refers to the form in which the dose is to be administered to the patient. The composition is generally administered as part of a formulation that includes nonmedical agents. Dosage forms may be solid, liquid or gaseous. Solid forms include, but are not limited to pills, capsules, tablets, gel caplets, softgels, lozenges, wafers etc.

As used herein and unless otherwise specified, the term "patient" refers to an animal, preferably a mammal, most preferably a human, who has been the object of treatment, observation or experiment. Preferably, the patient has experienced and/or exhibited at least one symptom of the disease or disorder to be treated and/or prevented. Further, a patient may not have exhibited any symptoms of the disorder, disease or condition to be treated and/prevented, but has been deemed by a physician, clinician or other medical professional to be at risk for developing said disorder, disease or condition.

As used herein and unless otherwise specified, the term "substantially pure" in reference to compounds or substances means a purity of at least 90%.

As used herein and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more therapeutic agents to a patient with such a disease or disorder. In some embodiments, the terms refer to the administration of a composition provided herein, with or without other additional active agents, after the onset of symptoms of the particular disease.

The present disclosure relates to novel methods of co-administration of high dose Vitamin $D_3$, heat shock proteins, glutathione, and kits provided for co-administration of these compositions, for the treatment of patients with chronic inflammation and chronic diseases, as herein described in detail.

Vitamin D is a group of fat-soluble secosteroid hormones responsible for increasing intestinal absorption of calcium, magnesium, and phosphate, and multiple other biological effects. In humans, the most important compounds in this group is Vitamin $D_3$ (also known as cholecalciferol). Vitamin $D_3$ is a true hormone that controls 3,000 out of 30,000 genes in the human body. Vitamin $D_3$ controls the immune response and inflammatory response systems (See for example Barbara Prietl, Gerlies Treiber, Thomas R. Pieber, and Karin Amrein. *Vitamin D and Immune Function*. Nutrients. 2013 July; 5(7): 2502-2521).

Heat shock proteins are a family of proteins that are produced by cells in response to exposure to stressful conditions. Heat shock proteins help the body's proteins maintain their 3-D shape while under stress such as trauma, acute, and chronic diseases. Heat shock proteins are found in all cellular organisms, from single celled organisms like microorganisms, to plants, fish, animals and within every cell in the human body. Heat shock proteins are key mediators of health and disease and have been shown to be essential molecules conserved through cellular evolution required for cells to survive the stresses encountered in the environment and in the tissues of the developing and aging organism. Heat shock proteins play an essential role in preventing the initiation of programmed cell death and repairing damage to the proteome, thus permitting resumption of normal cellular metabolism. Loss of heat shock protein is lethal either in the short-term in cases of acute stress or in the long-term when exposure to stress is chronic.

Twenty-seven kilo Dalton heat shock protein (Hsp27), also known as HspB 1; CMT2F; HMN2B; Hsp28; Hsp25; SRP27; HS.76067; HEL-S-102, encodes a member of the small heat shock protein (Hsp20) family of proteins. In response to environmental stress, the encoded protein translocates from the cytoplasm to the nucleus and functions as a molecular chaperone that promotes the correct folding of other proteins. This protein plays an important role in the differentiation of a wide variety of cell types. Expression of this gene is correlated with poor clinical outcome in multiple human cancers, and the encoded protein may promote cancer cell proliferation and metastasis, while protecting cancer cells from apoptosis. Mutations in this gene have been identified in human patients with Charcot-Marie-Tooth disease and distal hereditary motor neuropathy. (See the National Center for Biotechnology Information's Genes & Expression report at https://www.ncbi.nlm.nih.gov/gene/3315).

Sixty kilo Dalton heat shock protein (Hsp60), also known as HspD1; HLD4; CPN60; GROEL; Hsp65; SPG13; Hsp-60; HuCHA60), encodes a member of the chaperonin family. The encoded mitochondrial protein may function as a signaling molecule in the innate immune system. This protein is essential for the folding and assembly of newly imported proteins in the mitochondria. This gene is adjacent to a related family member and the region between the 2 genes functions as a bidirectional promoter. Several pseudogenes have been associated with this gene. Two transcript variants encoding the same protein have been identified for this gene. Mutations associated with this gene cause autosomal recessive spastic paraplegia 13. (See the National Center for Biotechnology Information's Genes & Expression report at https://www.ncbi.nlm.nih.gov/gene/3329).

Seventy kilo Dalton heat shock protein (Hsp70), also known as Hsp72; HspA1; Hps70I; Hsp70-1; Hsp70.1; Hsp70-1A; HEL-S-103): This intronless gene encodes a 70 kDa heat shock protein which is a member of the heat shock protein 70 family. In conjuction with other heat shock proteins, this protein stabilizes existing proteins against aggregation and mediates the folding of newly translated proteins in the cytosol and in organelles. It is also involved in the ubiquitin-proteasome pathway through interaction with the AU-rich element RNA-binding protein 1. The gene is located in the major histocompatibility complex class III region, in a cluster with two closely related genes which encode similar proteins. (See the National Center for Biotechnology Information's Genes & Expression report at https://www.ncbi.nlm.nih.gov/gene/3303).

Ninety kilo Dalton heat shock protein (Hsp90), also known as Hsp90AA1; EL52; HspN; LAP2; Hsp86; HspC 1; HspCA; Hsp89; LAP-2; Hsp89A; Hsp90A; Hsp90N; Hsp103; HspCAL1; HspCAL4; HEL-S-65p): The protein encoded by this gene is an inducible molecular chaperone that functions as a homodimer. The encoded protein aids in the proper folding of specific target proteins by use of an ATPase activity that is modulated by co-chaperones. Two transcript variants encoding different isoforms have been found for this gene. (See the National Center for Biotechnology Information's Genes & Expression report at https://www.ncbi.nlm.nih.gov/gene/3320).

The inventors have found a novel paradigm: heat shock proteins, previously known to be only intracellular molecular chaperones, can be found in the extracellular milieu where it has regulatory effects on immunocompetent cells. (See for example Hongying Zheng, Ganachari M. Nagaraja, Punit Kaur, Edwina E. Asea, and Alexzander Asea. *Chaperokine Function of Recombinant Hsp72 Produced in Insect Cells Using a Baculovirus Expression System Is Retained*. The Journal of Biological Chemistry Vol. 285, No. 1, pp. 349-356)

Glutathione is called the human body's master antioxidant. It is produced in nearly every cell of the human body to fight free radical oxygen species and oxidation. (See for example V. Lobo, A. Patil, A. Phatak, and N. Chandra. *Free Radicals, Antioxidants And Functional Foods: Impact On Human Health Pharmacogn*. Rev. 2010 July-December; 4(8): 118-126).

The inventors have surprisingly found that, when used in combination, Vitamin $D_3$, heat shock proteins, and glutathione are three of the most powerful anti-inflammatory and anti-oxidants in the human body. The inventors have found that the combination of Vitamin $D_3$, heat shock proteins, and glutathione also stimulates the immune response system to fight off infections by increasing the white blood cell count (CD4 and CD8 T-cell counts). The inventors have found that Vitamin $D_3$ heat shock proteins, and glutathione complement each other by helping the body's cells survive under stressful conditions instead of dying, thus reducing mortality rate, pain, suffering, and high medical/hospital/healthcare costs. This results in a better quality of life and lower medical expenses on an individual, state, national and global level.

Therefore, the present invention offers treatment options for many chronic diseases which presently have no treatment. The novel combination of Vitamin $D_3$ heat shock proteins, and glutathione provided by the present disclosure is advantageous over existing therapies, as it has very few minor, rare side effects such as vitamin D toxicity (rare, <1%) and pruritus.

In one embodiment of the present disclosure, the methods may comprise co-administering a first composition comprising Vitamin $D_3$, a second composition comprising heat shock proteins and optionally a third composition comprising glutathione to a patient.

In another embodiment, the first composition may comprise about 1,000 IU to about 150,000 IU of Vitamin $D_3$, the second composition may comprise about 100 mg to about 1,000 mg of heat shock proteins, and the third composition may comprise about 500 mg to 1,000 mg of glutathione.

In another embodiment, the Vitamin $D_3$ is substantially pure Vitamin $D_3$. The heat shock proteins may be selected from, but not limited to Hsp27; Hsp60; Hsp65; Hsp70; Hsp72; and Hsp90. One of ordinary skill in the relevant art would recognize that heat shock proteins function in a similar fashion and are classified as molecular chaperones. Preferably the heat shock protein is Hsp 60. More preferably the heat shock protein is Hsp 70. Most preferably the heat shock protein is Hsp72. The glutathione is substantially pure glutathione.

In another embodiment, the methods may comprise administering about 150,000 IU of Vitamin $D_3$ to the patient for about five days; administering about 50,000 IU of Vitamin $D_3$ to the patient weekly beginning on the 6th day of treatment; administering about 1,000 mg of heat shock proteins to the patient daily beginning on the 6th day of treatment; and optionally co-administering 1,000 mg of glutathione.

In another embodiment, the methods may comprise administering about 5,000 IU of Vitamin $D_3$ and about 500 mg of heat shock proteins to a patient daily for about two weeks; and optionally co-administering 1,000 mg of glutathione.

In another embodiment, the compositions of the described method may be co-administered to the patient orally. In another specific embodiment, the compositions may be swallowable, chewable, or dissolvable. The compositions may be in the form of a tablet, capsule or gel capsule.

In another embodiment of the present disclosure, the kits may comprise: a first composition comprising Vitamin $D_3$, a second composition comprising heat shock proteins, and an optional third composition comprising glutathione, wherein the first, second and third compositions are packaged for co-administration to a patient.

In another embodiment, the kits are packaged in various forms including blister packs. The kits may be packaged in blister packs that are sold together: blister packs containing a first composition comprising vitamin $D_3$, blister packs containing a second composition comprising heat shock proteins and optionally blister packs containing a third composition comprising glutathione.

In another embodiment, the kits may be packaged in blister packs containing a first composition comprising vitamin $D_3$, a second composition comprising heat shock proteins and optionally a third composition comprising glutathione, together in the same blister.

In yet another embodiment, the kits may be packaged in blister packs advertised as more effective if co-administered. The advertisements may consist of internet, print, and product packaging advertisements.

In another embodiment, the disclosure provides a method comprising providing the kits as described to a patient. The patient may include a patient who stays in a hospital while under treatment or a patient who receives treatment without being admitted to a hospital.

Finally, the present disclosure provides for a method of treating disease by administering to a patient the compositions described herein for the treatment of chronic inflammation and chronic diseases. Such diseases may include, but are not limited to, traumatic brain injury; concussion; congestive heart failure; coronary artery disease; heart attacks; stroke; chronic neurogenic disorders; arthritis; acute respiratory distress syndrome; community acquired pneumonia; ventilated associated pneumonia; dementia; Alzheimer's Disease; acute and chronic renal failure; multi-system organ failure; acute and chronic liver diseases, chronic obstructive pulmonary disease, acute and chronic pulmonary diseases, auto-immune diseases, cardiopulmonary arrest, and other chronic diseases of aging.

Other objectives, features and advantages of the present invention are apparent from the following specific Examples. The specific Examples, while indicating specific embodiments of the invention, are provided by way of illustration only.

EXAMPLES

Example 1

Glial Cell Culture

Glial cells were purchased from ATCC (DBTRG-05MG; CRL-2020) and were derived from the brain of a Caucasian women with glioblastoma. Cells were cultured in RPMI-1640 Medium (ATCC) supplemented with 10% fetal bovine serum, L-proline (30 mg/L), L-cystine (35 mg/L), HEPES (3.75 g/L), hypoxanthine (15 mg/L), adenosine triphosphate (1 mg/L), adenine (10 mg/L), thymidine (1 mg/L). Glial cells were subcultured at a ratio of about 1:4 every 2 to 3 days.

Example 2

Reagents

Vitamin $D_3$ (Cholecalciferol ≥298% by HPLC), Glutathione (US Pharmacopeia Reference Standard; γ-L-Glutamyl-L-cysteinyl-glycine) and Hydrogen peroxide ($H_2O_2$) solution (50 wt. % in $H_2O$, stabilized) were purchased from Sigma-Aldrich Chemicals (Rahway, N.J.).

Example 3

Preparation of Endotoxin-Free Hsp72

Endotoxin-free recombinant Hsp72 was produced using the baculovirus expression vector system (BEVS) and expressed in insect cells as described in Zheng H, Nagaraja G M, Kaur P, Asea E E, Asea A A. *Chaperokine function of recombinant Hsp72 produced in insect cells using a baculovirus expression system is retained*. Journal of Biological Chemistry 2010; 285(1): 349-356. Recombinant baculovirus transfer plasmids containing individual inserts (Hsp70) were transfected along with the linearized wild-type baculovirus (*Autographa californica* nuclear polyhedrosis virus, AcMNPV) DNA (home-made) into Sf9 cells. The transfection procedure was performed as described in Smith G E, Summers M D, Fraser M J. *Production of human beta interferon in insect cells infected with a baculovirus expression vector*. Molecular & Cell Biology 1983; 3(12): 2156-2165. Sf9 cells were seeded into T25 flasks at a density of 2.0×106 cells per flask.

After about 1 hour, media was removed and replaced with about 0.75 ml Grace's medium containing about 10% FBA. About 0.75 ml transfection buffer (25 mM HEPES, pH 7.1, 140 mM NaCl, 125 mM $CaCl_2$)) was added to a 1.5 ml polypropylene tube which contains about 1 µg of linearized AcMNPV DNA and about 2.5 µg baculovirus transfer vector. The cells were incubated at about 27° C. for about 4 hours following adding DNA solution dropwise to the Grace's medium in the flask. Medium was removed and replaced with about 5 ml BacVector Insect Cell Medium.

After about 6 days post-infection, medium was collected and recombinant virus was identified and purified by plaque assays. Recombinant viruses were plaque-purified three times to eliminate contamination by wild-type baculovirus. To confirm the recombinant virus containing corresponding Hsp72 gene, recombinant viral DNAs were isolated and examined for the correct gene insert by PCR. The two primers used for PCR verification of recombinant virus production were EcoRV-For (5'-CCATTGTAATGAGACGCAC-3' (SEQ ID NO: 11) and DOWN1629-Rev (5'-CTGTAAATCAACAACGCACAG-3' (SEQ ID NO: 21). Sf9 cells were infected with purified recombinant virus from each purified plaque at a multiplicity of infection (MOI) of 10.

After about 72 hours post infection at about 27° C., Sf9 cell culture was collected and added about 0.05 culture volume of Insect PopCulture Reagent (Novagen, San Diego, Calif.), followed by 4U Benzonase Nuclease per about 1 ml of the original culture volume. The mixture was inverted gently and incubated at about room temperature for about 15 min. The cell pellets were removed by centrifugation for about 20 min at 15,000 rpm (4° C.). For purification of His-tagged proteins, the supernatants were subjected to metal-chelation column chromatography using His-Bind resin (Novagen) equilibrated with column buffer (about 300 mM NaCl, about 50 mM sodium phosphate buffer, about 1 mM imidazole, about pH 8.0). The column was washed twice with about 10 ml of wash buffer (about 300 mM NaCl, about 50 mM sodium phosphate buffer, about pH 8.0) containing about 5 mM imidazole. The bound proteins were eluted with elute buffer (300 mM NaCl, 50 mM sodium phosphate buffer, pH 8.0) containing about 250 mM imidazole. Fractions containing Hsp70 proteins were further desalted and identified by Western Blot and Mass Spectrometry. Purified proteins were analyzed for endotoxin content using the Limulus amebocyte lysate assay (Cambrex). Protein concentration was detected by RC DC protein assay (Bio-Rad).

Example 4

Western Blot Analysis

The purity of Hsp72 was determined by resolving a 50-microgram protein on 10% SDS-PAGE gel and blotting it on PVDF membrane by Western transfer. The blot was blocked with 5% BSA in TBS with Tween-20 (TBST) and probed with primary antibodies against human Hsp72 (StressGen) and countered stained with secondary antibody (anti-mouse HRP (1:15000) (BD Pharmingen). Signals were detected on X-ray film after treatment with chemiluminiscent substrate (Pierce).

Example 5

In-Gel Digestion and LC-Mass Spectrometry

The purity of Hsp72 was determined by processing samples by in-gel digestion with trypsin. After reduction and alkylation, the gel pieces were digested overnight with sequencing grade trypsin (Promega) at about 37° C. The peptide samples were zip-tip cleaned with trifluroacetic acid (TFA) and acetonitrile mixture and dried in Speedvac. The samples were re-dissolved in about 0.1% TFA, fractionated and mass spectra was obtained by automated LC-MS/MS analysis (Agilent). CID data was searched against the SwissProt all species database, using the Agilent Spectrum Mill Server software (Rev A.03.03) installed on a HP Intel® Xeon™ dual processor server. Peak lists were created with the Spectrum Mill Data Extractor program with the following attributed: scans with the same precursor ±1.4 m/z were merged within a time frame of ±15 seconds. Precursor ions needed to have a minimum signal to noise value of 25. Charges up to a maximum of 7 were assigned to the precursor ion and the 12 C peak was determined by the Data Extractor. The SwissProt database was searched for tryptic peptides with a mass tolerance of 2.5 Da for the precursor ions and a tolerance of 0.7 Da for the fragment ions. Two missed cleavages were allowed. A Spectrum Mill autovalidation was performed first in the protein details followed by peptide mode using default values [Minimum scores, minimum scored peak intensity (SPI), forward minus reversed score threshold, and rank 1 minus rank 2 score threshold]. All protein hits found in a distinct database search by Spectrum Mill are non-redundant.

Example 6

Lactate Dehydrogenase (LDH) Cell Death Assay

Cell death was measured by the CytoTox 96 Non-Radioactive Cytotoxicity Assay according to the manufacturer's instructions (Promega, Madison, Wis.). Culture medium (500 µl) was recovered from and incubated for about 30 min in the dark with a buffer containing NAD+, lactate, and tetrazolium. Lactate Dehydrogenase (LDH) converts lactate to pyruvate, generating NADH which reduces tetrazolium (yellow) to formazan (red), which is detected by fluorescence (490 nm). LDH release, a marker for cell death, was expressed as a percentage of the LDH in the medium over the total LDH.

Example 7

Statistical Analysis

Data was analyzed using a two-tailed t-test after applying ANOVA to the data. Differences were considered significant when $p<0.01$.

Example 8

Pre- and Post-Treatment with Vitamin $D_3$+Heat Shock Proteins

Glia cells ($10^6$ cells) were plated in triplicates in 6-well plates. About twenty-four hours later cells were exposed to [2] control (PBS) or [3] $H_2O_2$ (0.25M) about 30 minutes before or [4] $H_2O_2$ (0.25M) about 30 minutes after treatment with [1] control (PBS) or Vitamin $D_3$ or heat shock protein 72 (Hsp72) or Vitamin D+Hsp72. Percentage cell survival was calculated about 24 hours later using LDH assay. Data is represented as percentage cells survival ±SD and is the sum of 3 independently performed experiments.

TABLE 1

Pre- and post-treatment of Glia cells with Vitamin $D_3$ + Hsp72 results in the synergistic protection against exposure to $H_2O_2$.

| | Percentage Cell Survival (% ± SD) before or after exposure of the following compounds | | |
|---|---|---|---|
| Treatment[1] | Control[2] | $H_2O_2$ Given 1st (30 min after $H_2O_2$ Given, mimics acute injury)[3] | $H_2O_2$ Given Last (30 min before $H_2O_2$ given/pre-treatment))[4] |
| Control (PBS) | 95.45 ± 5.1 | 5.39 ± 3.7 | 8.77 ± 6.2 |
| Vitamin $D_3$ | 94.64 ± 4.6 | 15.27 ± 7.4* | 28.56 ± 8.9* |
| Hsp72 | 96.88 ± 3.8 | 31.85 ± 9.2* | 48.54 ± 6.3* |
| Vitamin $D_3$ + Hsp72 | 97.22 ± 4.7 | 82.11 ± 6.1* | 96.50 ± 3.3* |

Example 9

Pre- and Post-Treatment with Vitamin $D_3$+Heat Shock Proteins+Glutathione

Glia cells ($10^6$ cells) were plated in triplicates in 6-well plates. About twenty-four hours later cells were exposed to [2] control (PBS) or [3] $H_2O_2$ (0.25M) about 30 minutes before or [4] $H_2O_2$ (0.25M) about 30 minutes after treatment with [1] control (PBS) or Vitamin $D_3$ (1/5) or Hsp72 (1/5) or Glutathione (200 mg/ml) or Vitamin $D_3$+Hsp72 or Vitamin $D_3$+Hsp72+Glutathione. Percentage cell survival was calculated about 24 hours later using LDH assay. Data is represented as percentage cells survival ±SD and is the sum of 4 independently performed experiments.

TABLE 2

Treatment with Vitamin $D_3$ + Hsp72 + Glutathione results in the complete protection of Glia cells from oxidative radical-induced cell death at lower concentrations than Vitamin $D_3$ + Hsp72.

| | Percentage Cell Survival (% ± SD) before or after exposure of the following compounds | | |
|---|---|---|---|
| Treatment[1] | Control[2] | $H_2O_2$ (added 30 min before)[3] | $H_2O_2$ (added 30 min after)[4] |
| Control (PBS) | 96.37 ± 5.1 | 4.21 ± 2.6 | 3.38 ± 1.5 |
| Vitamin $D_3$ (1/5) | 97.28 ± 4.3 | 10.36 ± 2.3* | 12.68 ± 3.5* |
| Hsp72 (1/5) | 95.48 ± 5.1 | 21.57 ± 5.4* | 32.68 ± 7.5* |
| Glutathione | 96.99 ± 3.6 | 15.85 ± 4.5* | 26.45 ± 6.8* |
| Vitamin $D_3$ + Hsp72 | 98.94 ± 4.1 | 51.96 ± 7.2* | 72.25 ± 6.5* |
| Vitamin $D_3$ + Hsp72 + Glutathione | 98.94 ± 4.1 | 95.74 ± 5.7* | 98.15 ± 4.1* |

Example 10

Pre- and Post-Treatment with Vitamin $D_3$

Glia cells ($10^6$ cells) were plated in triplicates in 6-well plates. About twenty-four hours later cells were exposed to [2] control (PBS) only or [3] $H_2O_2$ (0.25M) about 30 minutes before or [4] $H_2O_2$ (0.25M) about 30 minutes after treatment with various concentrations of Vitamin $D_3$. Percentage cell survival was calculated about 24 hours later using LDH assay. Data is represented as percentage cells survival ±SD and is the sum of 3 independently performed experiments.

TABLE 3

Pre- and Post-Treatment of Glia Cells with Vitamin $D_3$ Protects Against Exposure to $H_2O_2$.

| | Percentage Cell Survival (% ± SD) before or after exposure of the following compounds | | |
|---|---|---|---|
| Treatment[1] | Control (PBS)[2] | $H_2O_2$ Given (30 min before treatment with Vitamin D)[3] | $H_2O_2$ given (30 min after treatment with Vitamin D)[4] |
| Control (PBS) | 92.37 ± 3.3 | 5.39 ± 2.7 | 4.63 ± 1.2 |
| Vitamin $D_3$ (5 ng/ml) | 96.89 ± 4.5 | 6.22 ± 2.8 | 9.75 ± 3.6 |
| Vitamin $D_3$ (25 ng/ml) | 98.56 ± 7.9 | 10.18 ± 2.2* | 13.09 ± 2.9* |
| Vitamin $D_3$ (50 ng/ml) | 91.18 ± 6.8 | 15.27 ± 4.4* | 28.56 ± 3.9* |
| Vitamin $D_3$ (75 ng/ml) | 95.82 ± 6.2 | 22.94 ± 3.8* | 35.14 ± 88* |
| Vitamin $D_3$ (100 ng/ml) | 97.41 ± 8.4 | 28.99 ± 6.9* | 60.11 ± 7.2* |

Example 11

Dosages, Dosage Forms, and Treatment Protocols

The present disclosure provides for a method of treating disease by administering to a patient the compositions described herein for the treatment of chronic inflammation and chronic diseases. Vitamin $D_3$ may be combined with heat shock proteins. Heat shock proteins suitable for combination with Vitamin $D_3$ with the present disclosure include Hsp27, Hsp60, Hsp65, Hsp70, Hsp72 and Hsp90. The Vitamin $D_3$ and HSP may be manufactured as tablets in pill-form and gel-form solid blister packs according to manufacturing protocols known to those of ordinary skill in the relevant art. Vitamin $D_3$ and glutathione are available commercially in oral dosages.

An embodiment of the present disclosure provides substantially pure Vitamin $D_3$ in combination with twenty-seven kilo Dalton heat shock protein (Hsp27).

An embodiment of the present disclosure provides substantially pure Vitamin $D_3$ in combination with sixty kilo Dalton heat shock protein (Hsp60).

An embodiment of the present disclosure provides substantially pure Vitamin $D_3$ in combination with sixty-five kilo Dalton heat shock protein (Hsp65).

An embodiment of the present invention provides substantially pure Vitamin $D_3$ in combination with seventy kilo Dalton heat shock protein (Hsp70).

An embodiment of the present invention provides substantially pure Vitamin $D_3$ in combination with seventy-two kilo Dalton heat shock protein (Hsp72).

An embodiment of the present invention provides substantially pure Vitamin $D_3$ in combination with ninety kilo Dalton heat shock protein (Hsp90).

The oral dosages indicated in Table 4 are indicative of loading and maintenance dosages while a patient is in the hospital or under a physician's care. For example, an embodiment of the invention provides that a patient may be administered a loading dosage of Vitamin $D_3$ daily at 150,000 (IU), Hsp daily at 1,000 mg and glutathione at 1,000 mg daily for five days, then maintenance dosages of Vitamin $D_3$ at 50,000 IU weekly, Hsp daily at 1,000 mg and glutathione daily at 500 mg for two weeks.

In yet another embodiment, a patient may be administered a loading dosage of Vitamin $D_3$ daily at 150,000 IU, Hsp daily at 1,000 mg and glutathione at daily 500 mg for seven days, then maintenance dosages of Vitamin $D_3$ at 50,000 IU weekly, Hsp daily at 500 mg, and glutathione daily at 500 mg for four weeks.

In yet another embodiment, a patient may be administered a loading dosage of Vitamin $D_3$ daily at 50,000 IU, Hsp daily at 1,000 mg and glutathione daily at 1,000 mg for seven days: then maintenance dosages of Vitamin $D_3$ at 50,000 IU weekly. Hsp daily at 500 mg and glutathione daily at 50 mg for four weeks.

In yet another embodiment, a patient may be administered a loading dosage of Vitamin $D_3$ at 50,000 IU daily, Hsp daily at 500 mg and glutathione daily at 500 mg for ten days; then maintenance dosages of Vitamin $D_3$ at 5,000 IU daily, Hsp daily at 500 mg and glutathione daily at 500 mg for four weeks.

In yet another embodiment, a patient may be administered a loading dosage of Vitamin $D_3$ daily at 50,000 IU. Hsp daily at 500 mg and glutathione daily at 500 mg for seven days; then maintenance dosages of Vitamin $D_3$ daily at 5,000 IU, Hsp daily at 500 mg and glutathione at daily at 500 mg for two weeks.

In yet another embodiment, a patient may be administered a loading dosage of Vitamin $D_3$ daily at 50,000 IU, Hsp daily at 500 mg and glutathione daily at 500 mg for seven days; then maintenance dosages of Vitamin $D_3$ daily at 2,000 IU, Hsp daily at 500 mg and glutathione daily at 500 mg for four weeks.

TABLE 4

Treatment Protocol

| Vitamin $D_3$, HSP and Glutathione to administered daily/weekly | | | |
|---|---|---|---|
| Vitamin $D_3$ (IU) | HSP (mg) | Glutathione (mg) | Glutathione (mg) |
| 150,000 | 1,000 | 1,000 | 500 |
| 50,000 | 1,000 | 1,000 | 500 |
| 50,000 | 500 | 1,000 | 500 |
| 5,000 | 1,000 | 1,000 | 500 |
| 5,000 | 500 | 1,000 | 500 |
| 2,000 | 1,000 | 1,000 | 500 |
| 1,000 | 500 | 1,000 | 500 |

The compositions of the present disclosure may be oral dosage forms, including tablets, capsules and gel capsules. Choice in dosage form promotes ease of administration and compliance with dosing regimens. The compositions of the present disclosure suitable for oral administration include tablets, caplets, and capsules. The dosage form contains a predetermined amount of the active agent and can be prepared by methods well known to those skilled in the pharmaceutical art (for example see Remington's Pharmaceutical Sciences, 18th ed., (1990)).

Typical oral dosage forms of the present invention are prepared by blending in intimate mixture active ingredients with at least one excipient according to conventional pharmaceutical compounding techniques. Excipients may be selected from a wide variety of forms depending on the form of preparation desired for administration. For example, solid oral dosage forms, include but not limited to for example, excipients suitable for use in powders, tablets, capsules, and caplets include starch, sugar, microcrystalline cellulose, diluents, granulating agents, lubricants, binders, and disintegrating agents.

A tablet may be prepared, for example, by compression or molding. The compressed tablet is prepared in a suitable machine using an active ingredient or ingredient(s) and optionally mixed with an excipient, which may be powder or granules. Molded tablets are then produced by molding the active compound or compounds in a suitable mixture with a moistened inert liquid diluent. If desired, tablets may be coated using standard aqueous or non-aqueous techniques. Such dosage forms can be prepared by any method known to one of skill in the art.

Examples of excipients that can be used in oral dosage forms of the invention include binders, fillers, disintegrants, and lubricants, but is not limited to these. Excipients for the use in active compositions dosage forms include for example, corn starch, potato starch, or other starches, gelatin, gum arabic, such as natural and synthetic gums, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, including, but microcrystalline cellulose, and mixtures thereof, but is not limited to these.

The above examples are set forth to aid in the understanding of the disclosure and are not intended and should not be construed to limit in any way the disclosure set forth or the claims which follow hereafter. Although illustrated and herein described with reference to certain specific embodiments, the present disclosure is nevertheless not intended to be limited to the details shown, but various modifications may be made therein without departing from the spirit of the disclosure.

REFERENCES

Asea, A., DeMaio, A., eds. Potent Mediators of Inflammation and Immunity, series eds. A. Asea, S. K. Calderwood.

Dordrecht, The Netherlands: Springer Nature. Vol. 1, 2007; 357 pp. ISBN 978-1-4020-5585-0. http://www.springer.com/us/book/9781402055843

Calderwood, S. K., Sherman, M. Y., Ciocca, D., eds, Heat Shock Proteins in Cancer, series eds. A. Asea, S. K. Calderwood. Dordrecht, The Netherlands: Springer Nature. Vol. 2, 2007; 398 pp. ISBN 978-1-4020-6400-5. http://link.springer.com/book/10.1007%2F978-1-4020-6401-2

Asea, A., Brown, I. R., eds. Heat Shock Proteins and the Brain: Implications for Neurodegenerative Diseases and Neuroprotection, series eds. A. Asea, S. K. Calderwood. Dordrecht, The Netherlands: Springer Nature. Vol. 3, 2008; 373 pp. ISBN 978-1-4020-8231-3. http://www.springer.comnus/book/9781402082306

Calderwood, S. K., Pockley, A. G., Santoro, G., eds. Prokaryotic and Eukaryotic Heat Shock Proteins in Infectious Disease, series eds. A. Asea, S. K. Calderwood. Dordrecht, The Netherlands: Springer Nature. Vol. 4, 2009; 311 pp. ISBN 978-90-481-2976-8. http://www.springer.com/us/book/9789048129751

Asea, A., Pedersen, P. K., eds. Heat Shock Proteins and Whole Body Physiology, series eds. A. Asea, S. K. Calderwood. Dordrecht, The Netherlands: Springer Nature. Vol. 5, 2010; 429 pp. ISBN 978-90-481-3381-9. http:/www.springer.com/us/book/9789048133802

Tanguay, R. M, Hightower, L. E., eds. The Big Book on Small Heat Shock Proteins. series eds. A. Asea, S. K. Calderwood. Dordrecht, The Netherlands: Springer Nature. Vol. 8, 2015; 682 pp. ISBN 978-3-319-16077-1. http://www.springer.com/us/book/9783319160764

Asea, A., Almasoud, N. N, Krishnan, K., Kaur, P., eds. Heat Shock Protein-Based Therapies, series eds. A. Asea, S. K. Calderwood. Dordrecht, The Netherlands: Springer Nature. Vol. 9, 2015; 375 pp. ISBN 978-3-319-17211-8. http://www.springer.com/us/book/9783319172101

Asea, A., Kaur, P., eds. Heat Shock Proteins in Veterinary Research and Medicine, series eds. A. Asea, S. K. Calderwood. Dordrecht, The Netherlands: Springer Nature. Vol. 12, 2018, 398 pp. ISBN 978-3-319-73377-7. http://www.springer.com/us/book/9783319733760

Asea, A., Kaur, P., eds. Regulation of Heat Shock Protein Responses, series eds. A. Asea, S. K. Calderwood. Dordrecht, The Netherlands: Springer Nature. Vol. 15, 2018, 501 pp. ISBN 978-3-319-74715-6. http://www.springer.com/us/book/9783319747149

Ahmed, Y., Griggs, D. D., Danner, O. K., Matthews, R., Wilson, K. L. Worsening severity of vitamin D deficiency is associated with increased length of stay, surgical intensive care unit cost, and mortality rate in surgical intensive care unit patients. The American Journal of Surgery July 2012 Volume 204, Issue 1, Pages 37-43.

What is claimed is:

1. A method of treating traumatic brain injury in a patient comprising co-administering to the patient a first composition consisting essentially of Vitamin $D_3$ and a second composition consisting essentially of heat shock proteins.

2. The method according to claim 1, wherein the first composition consists essentially of about 1,000 IU to about 150,000 IU of Vitamin $D_3$.

3. The method according to claim 1, wherein the second composition consists essentially of about 100 mg to about 1,000 mg of heat shock proteins.

4. The method according to claim 1, wherein:
   (i) about 150,000 IU of Vitamin $D_3$ is administered to the patient for about five days;
   (ii) about 50,000 IU of Vitamin $D_3$ is administered to the patient weekly beginning on the $6^{th}$ day of treatment; and
   (iii) about 1,000 mg of heat shock proteins is administered to the patient daily beginning on the $6^t$ day of treatment.

5. The method according to claim 1, wherein:
   (i) about 5,000 IU of Vitamin $D_3$; and
   (ii) about 500 mg of heat shock proteins
is administered to the patient daily for about two weeks.

6. The method according to claim 1, wherein the heat shock proteins is selected from the group consisting of twenty-seven kilo Dalton heat shock protein (Hsp27); sixty kilo Dalton heat shock protein (Hsp60); sixty-five kilo Dalton heat shock protein (Hsp65); seventy kilo Dalton heat shock protein (Hsp70); seventy-two kilo Dalton heat shock protein (Hsp72); and ninety kilo Dalton heat shock protein (Hsp90).

7. The method according to claim 1, wherein the method of treating further comprises administering to the patient a composition comprising glutathione.

8. The method according to claim 7, wherein the composition consists essentially of about 500 mg to about 1,000 mg of glutathione.

9. The method according to claim 1, wherein the dosage form is an oral dosage form.

10. The method according to claim 9, wherein the dosage form is a tablet, capsule or gel capsule.

* * * * *